United States Patent
Pollock (10) Patent No.: US 10,548,615 B2
(45) Date of Patent: Feb. 4, 2020

(54) C-TOURNIQUET

(71) Applicant: James Eric Pollock, Rockville, MD (US)

(72) Inventor: James Eric Pollock, Rockville, MD (US)

(*) Notice: Subject to any disclaimer, the term of this patent is extended or adjusted under 35 U.S.C. 154(b) by 0 days.

(21) Appl. No.: 14/565,809

(22) Filed: Dec. 10, 2014

(65) Prior Publication Data
US 2016/0045203 A1    Feb. 18, 2016

Related U.S. Application Data

(60) Provisional application No. 62/037,301, filed on Aug. 14, 2014.

(51) Int. Cl.
*A61B 17/135*    (2006.01)
*A61B 17/132*    (2006.01)

(52) U.S. Cl.
CPC .......... *A61B 17/135* (2013.01); *A61B 17/132* (2013.01); *A61B 17/1325* (2013.01)

(58) Field of Classification Search
CPC . A61B 17/132; A61B 17/1325; A61B 17/135; A61B 2017/12004
USPC .......... 606/158, 201, 203, 204, 205
See application file for complete search history.

(56) References Cited

U.S. PATENT DOCUMENTS

| | | | |
|---|---|---|---|
| 3,463,157 A * | 8/1969 | Hunt | A61D 1/00 128/97.1 |
| 5,026,379 A * | 6/1991 | Yoon | A61B 17/12013 606/141 |
| 5,312,350 A | 5/1994 | Jacobs | |
| D453,862 S * | 2/2002 | Cormier | F23Q 25/00 D28/55 |
| 2006/0212049 A1* | 9/2006 | Mohiuddin | A61B 17/083 606/151 |
| 2008/0319473 A1* | 12/2008 | Rosenbaum | A61B 17/1325 606/201 |
| 2009/0032050 A1 | 2/2009 | Defenbaugh et al. | |
| 2010/0042138 A1* | 2/2010 | Duelo Riu | A61H 7/006 606/204 |
| 2013/0256345 A1 | 10/2013 | Larkin | |
| 2014/0276600 A1 | 9/2014 | Foster et al. | |

(Continued)

FOREIGN PATENT DOCUMENTS

CN      2577772 Y    10/2003

OTHER PUBLICATIONS

'Rod' definition from Merriam-Webster dictionary accessed Feb. 12, 2019.*

(Continued)

*Primary Examiner* — Katherine M Shi
(74) *Attorney, Agent, or Firm* — Staas & Halsey LLP (57) ABSTRACT

A blood vessel compression device including a C-shaped spring and a clamp at an end of the spring to compress a blood vessel. The clamp may have a flat shaped cross section or spatulate cross section with an edge where the edge confronts a blood vessel to compress it. The clamp may have a channel and a sac inflatable with air to compress the blood vessel. The device may be positioned on body to clamp an external jugular vein or cephalic vein for cannula insertion. The C-shaped spring may be spaced from a front of the neck to not compress a windpipe of the neck.

17 Claims, 11 Drawing Sheets

(56) References Cited

U.S. PATENT DOCUMENTS

2015/0080942 A1* 3/2015 Garrison .............. A61B 8/4227
606/202

OTHER PUBLICATIONS

McPheeters, "Central Venous Access Via External Jugular Vein Technique", *Medscape*, Updated Jan. 16, 2013, 2 pp.
Shlamovitz, "External Jugular Vein Cannulation", *Medscape*, Updated May 22, 2013, 4 pp.

* cited by examiner

Section A-A'

FIG.4

Section B-B'

Section C-C'

C-TOURNIQUET

CROSS-REFERENCE TO RELATED APPLICATIONS

This application claims the benefit of U.S. Provisional Application Ser. No. 62/037,301, filed Aug. 14, 2014, the disclosure of which is incorporated herein by reference.

BACKGROUND OF THE INVENTION

1. Field of the Invention

The human external jugular vein (EJV) is a large vein used in pre-hospital medicine for venous access when the emergency medical technician (EMT) is unable to find another peripheral vein. It may also be used in an emergency or non-emergency setting where another peripheral vein cannot be located. It may be used in an unresponsive or an alert patient.

2. Description of the Related Art

SUMMARY OF THE INVENTION

Inserting an IV for Intravenous therapy (IV or iv therapy in short) is the infusion of liquid substances directly into a vein. Inserting an IV into the EJ vein may be difficult due to the patient's body habit's or build or during an emergency, such as a cardiac arrest, hemorrhage or shock.

Often the patient is placed in the Trendelenburg position where the body is laid flat on the back (supine position) with the feet higher than the head by 15-30 degrees, so the head is down. The patient is instructed to "bear down" or perform the Valsalva maneuver in an effort to dilate the vein. The Valsalva maneuver is a moderately forceful attempted exhalation against a closed airway, usually done by closing one's mouth, pinching one's nose shut while pressing out as if blowing up a balloon. This may not be indicated or may even be harmful in certain cases, such as congestive heart failure. Further the patient may not be cooperative or able to understand the instructions. Currently the only other way to dilate the EJ vein is with thumb pressure which makes the process of IV insertion technically more difficult and time consuming.

The cephalic vein (ECV), an external type vein, passing across the shoulder anterior aspect of the shoulder may also be used for IV therapy in some situations.

The IV procedure can be done by EMTs (Emergency Medical Technician) at the scene of an accident, or by a nurse or by a doctor in an office or hospital setting.

What may be needed is a device that can quickly and easily placed on the patients neck without choking to dilate the EJ vein to allow easy insertion of an IV needle.

What may be needed is a device that can quickly and easily placed on the shoulder at about the mid-clavicular line or more proximal to dilate the CV vein to allow easy insertion of an IV needle.

What may be needed is a device that may be used to apply unilateral or bilateral pressure to the EJ vein or CV vein as needed.

Sometimes additional pressure may needed for some patients to increase dilation and what may be needed is a device that can increase pressure after application to a maximal pressure of about 90 mmHG, under a pressure that may cause carotid artery compression when on the neck.

DETAILED DESCRIPTION OF THE PREFERRED EMBODIMENTS

Below and in conjunction with the figures will be described an external C-tourniquet or C-clamp that may be used to put pressure on human body veins, such as the external jugular (EJ) vein and the cephalic vein. When applied to the EJ vein the C-tourniquet does not choke the patient and leaves room for quick and easy IV therapy (or access) via the EJ vein.

Figure 1:
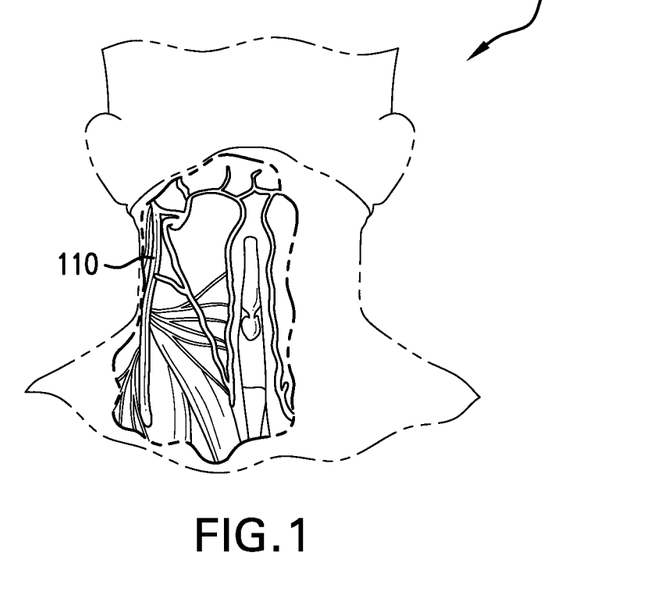
FIG. 1 shows the structure of the human throat showing location of the external jugular vein (EV).
Figure 2:
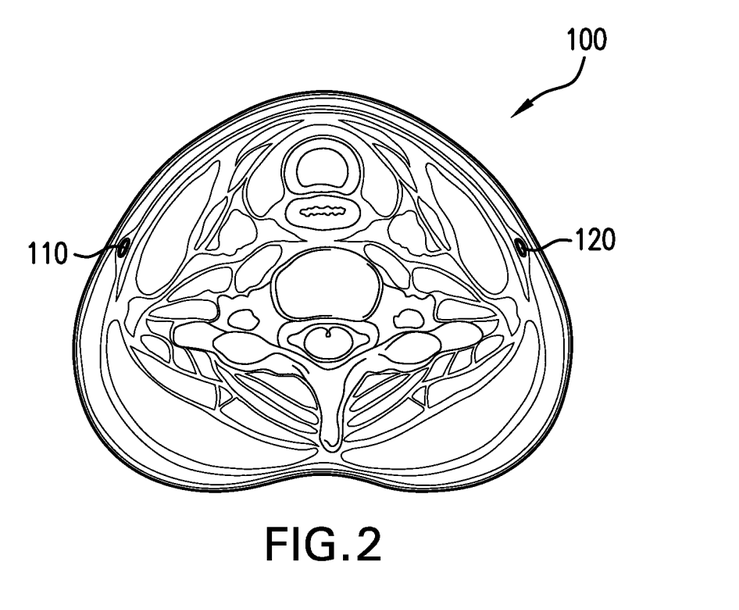
FIG. 2 is a cross section view of the neck showing the location of the external jugular vein.

As shown in FIG. 1, the neck 100 includes two external jugular veins 110 and 120 located on each side of the neck 100 and running vertically between the jaw and the collar bone. The veins 110 and 120, as shown in FIG. 2, are positioned just under the skin 200 of the neck 100.

Figure 3:
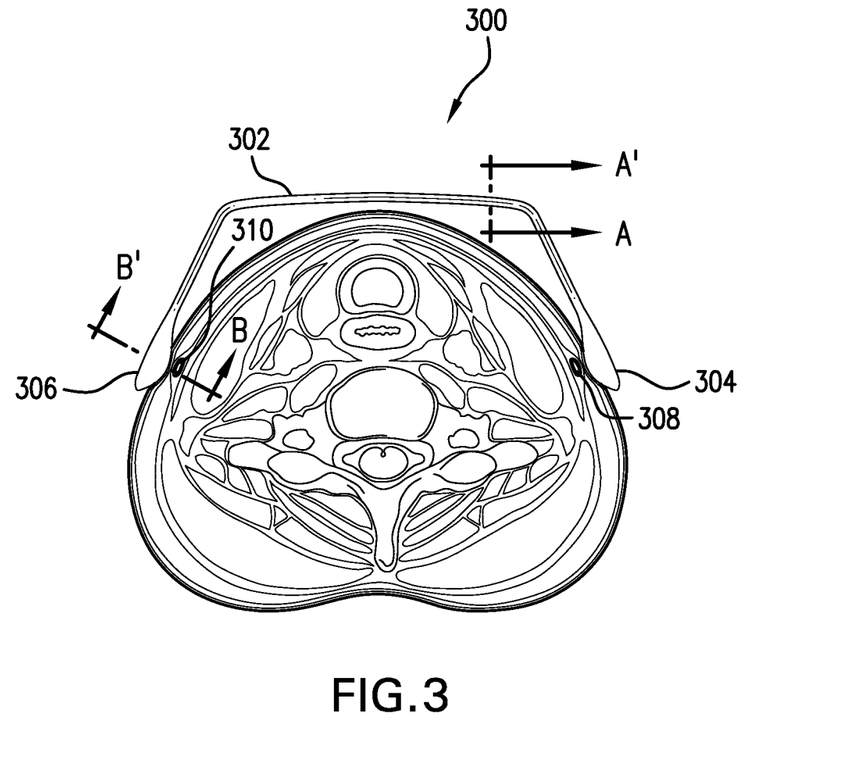
FIG. 3 depicts an external jugular vein device positioned to apply pressure.

FIG. 3 depicts a first embodiment of the C-tourniquet 300, it may preferably be a single piece structure made of plastic or metal as discussed below. The device 300 may have a spring member 302 and two clamp members 304 and 306. As can be seen, the clamp members 304 and 306 apply pressure to the EJ veins 308 and 310. The cross-section A'-A of the spring member 302 and that cross-section B'-B of one of the clamp members 306 of the device 300 are shown in FIGS. 4 and 5.

Figure 4:
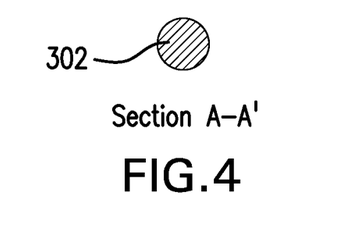
FIGS. 4 and 5 show cross-sections of spring and clamp members of FIG. 3.

As can be seen the cross-section of the spring member 302 may be round as depicted in FIG. 4 but may be oval, rectangular or some other shape. The spring member 302 imparts a closing force to the clamp members 302 and 304 to push them toward each other.

Figure 5:
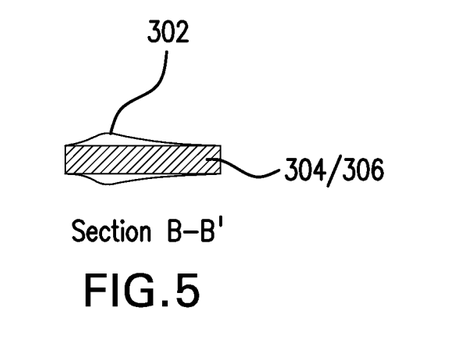

The cross-section of the clamp member 306, as depicted in FIG. 5 may be a flattened oval where one of the "flat" and "edge" sides confronts the neck. The spring member when it joins the clamp member is shown in dashed lines. The clamp members may have some other shape, such as round, oval, rectangular, etc. such that a non-penetrating shape is provided that can apply pressure to the veins without causing undue discomfort to the patient.

Figure 6:
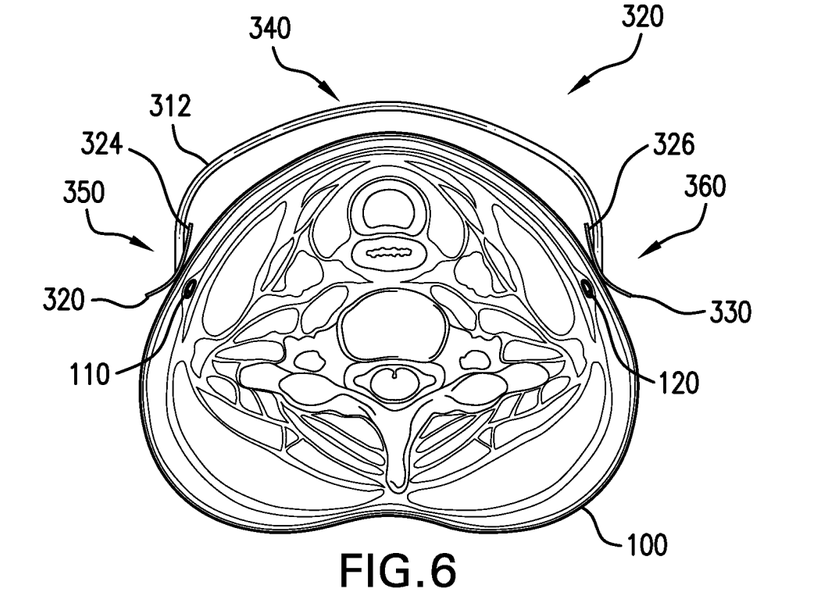
FIG. 6 depicts another external jugular vein u-shaped device positioned to apply pressure.

Another embodiment of the jugular vein tourniquet or clamp 320, as shown in FIG. 6, includes a spring member 312 and at least one clamp member where two clamp members 324 and 326 are shown. The clamp 320 may be preferably of disposable plastic as one piece, which could be made by injection molding. The spring member 312 may be of a circular cross section, although it may be another shape, such as an oval or rectangle, and may be tapered from the center 340 to the tips 350 and 360 to provide a variable spring force as the clamp 320 is opened. The radius of the spring member may such that the spring member reaches across the neck 100. Each of the clamp members 324 and 326 is shown with a circular convex type shape although the shape and size may be more like the pad of a finger, such as the thumb, with a curved center part having a low curvature like the finger pad and the ends with a higher curvature like the sides of the finger. The clamp members 324 and 326 may have a rectangular cross section where the side 370 toward the skin may have a surface that prevents slipping, such as a cross-hatched relief pattern surface. Although the cross-section of the clamp member may be rectangular in cross-section, the side of the clamp member away from the skin may be flat or curved.

During application of the clamp or C-tourniquet 300/320, where 320 of FIG. 6 will be used as an example, the user may place one of the clamp members, such as 326, on the skin over one of the veins, such as vein 110. The spring member 312 is then stretched against its spring force and the other clamp member 330 may be positioned on the skin over the other vein 120. The spring force of the clamp member 330 may be released and the clamp members 320 and 330 compress the part of the neck 100 where the vein 110 and 120 are located closing the veins.

FIG. 6, with some exaggeration for illustration purposes, shows a u-shaped clamp or tourniquet 320 compressing and closing the veins 110 and 120. Once the veins are closed they dilate due to the increased blood pressure on the upstream side of the clamp. The user can then use both hands as needed to cannulate the patient via one of the dilated veins.

Figure 7:
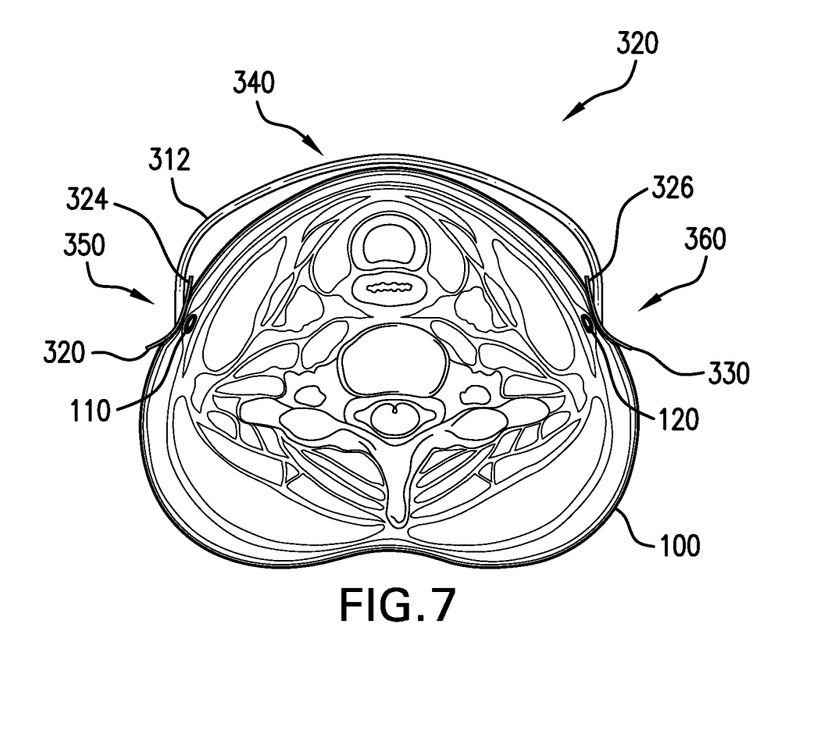
FIG. 7 shows the external jugular vein device of FIG. 6 compressing the external jugular veins.

FIG. 7 depicts the device of FIG. 6 as applied to the neck 100 showing the veins 110 and 120 compressed shut, which will close the veins to dilate them.

The clamp may be removed by pulling the spring member 310 away from the neck 100 after one of the veins has been cannulated or accessed.

The size of human necks vary from small, such as an infant, to large in an adult. It preferable that the clamp or tourniquet 300 (or 320) have several sizes, such as small, medium and large.

Figure 8:
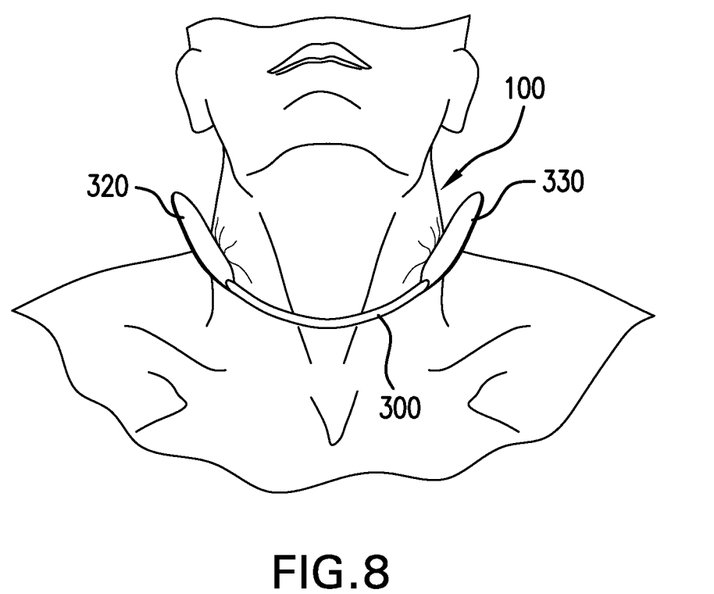
FIG. 8 shows a frontal neck view of the clamp 300 when applied.
Figure 9:
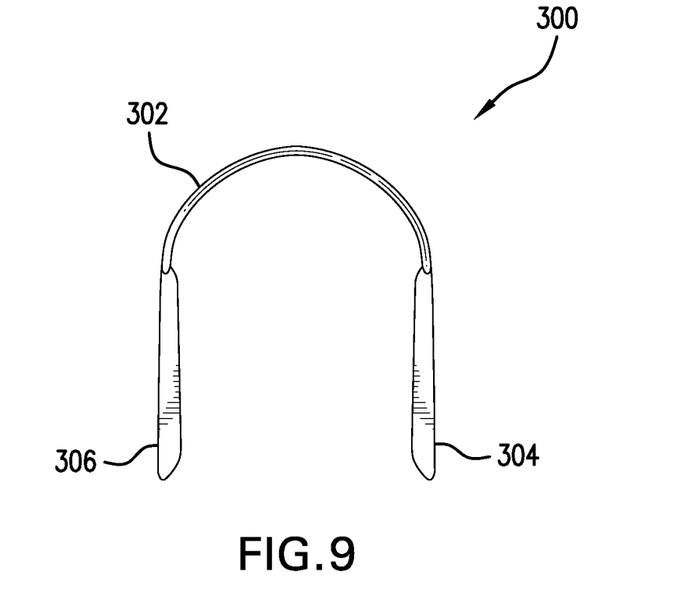
FIG. 9 shows the clamp 300 when not applied to the neck.

As shown in FIG. 8, the clamp 300 and clamp members 320 and 330 are positioned to compress the lateral aspects of the neck 100. The clamp 300 may be positioned where the vein superficially passes at the base of the neck 100. The clamp or C-tourniquet may be positioned close to the collar bone FIG. 9 shows the C-tourniquet or clamp 300 when not applied to a patient. As can be seen the device 300 is U-shaped or C-shaped when the spring member 310 is not under expansion tension.

Figure 10:
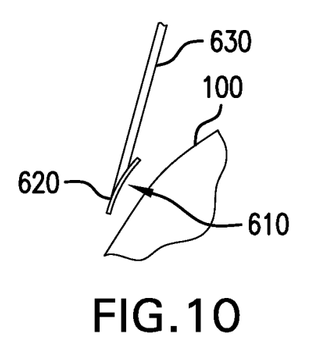
FIG. 10 depicts a clamp member 620 aligned at an angle with respect to a clamp tip 630.

FIGS. 6 and 7 shows the clamp members 320 and 330 with a cup axis somewhat aligned with the direction of the direction of the tips 350 and 360. FIG. 10, depicts an alternate embodiment where the cup 610 of the clamp member 620 may be aligned to the side so that it faces the neck 100 and may be at an angle with respect to the tip 630.

Figure 11A:
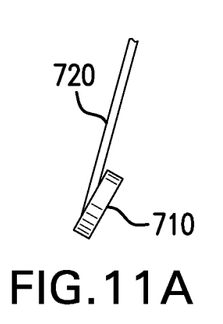
FIGS. 11A and 11B show a circular pad type clamp member 710.
Figure 11B:
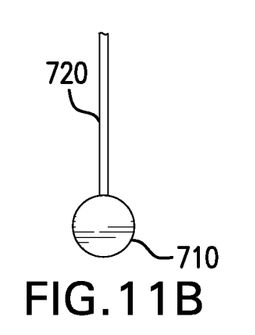

FIGS. 11A and 11B show views of another embodiment where the clamp member 710 may be like a miniature padded ear headphone and has an aspect with respect of the tip 720 like in FIG. 10. The clamp member 710 is shown as circular, but may be some other shape, such as oval or rectangular.

Figure 12A:
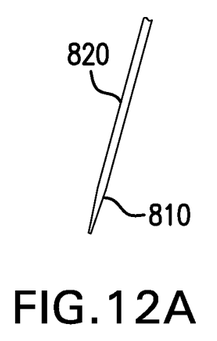
FIGS. 12A and 12B shows a tip flattened to for a clamp member.
Figure 12B:
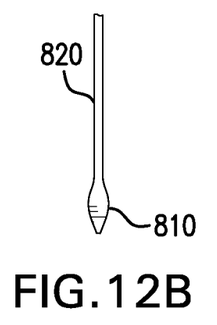

FIGS. 12 and 12B show a further embodiment where the tip of the clamp member 810 may be a flattened portion of the tip 820.

Figure 13:
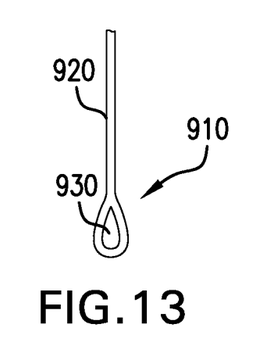
FIG. 13 illustrates a loop shaped clamp member.

FIG. 13 shows a tear drop shaped clamp member 910 at the end of a tip 920 where the clamp member 910 may be a plastic loop with an open space 930 in the center.

The clamp member can also be the end of a round or oval cross-section tip as it tapers to an end so that it occupies as little space of the neck 100 as possible. In addition the clamp need not be tapered from the center 340 to the tips 350 and 360 but may be of a constant cross-section.

Although the clamp 300 has been described with respect to use with the external jugular vein, it can also be used with the cephalic vein which runs across the front of the shoulder to allow venous access and may be threaded into the superior vena cava or central venous circulation. This may be done using the EV or CV.

Figure 14:
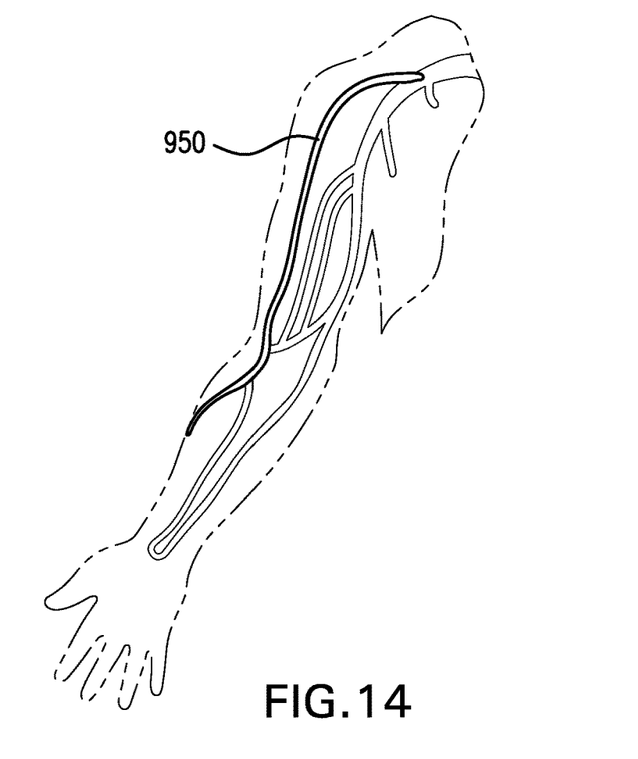
FIG. 14 shows the veins in the shoulder and arm.
Figure 15:
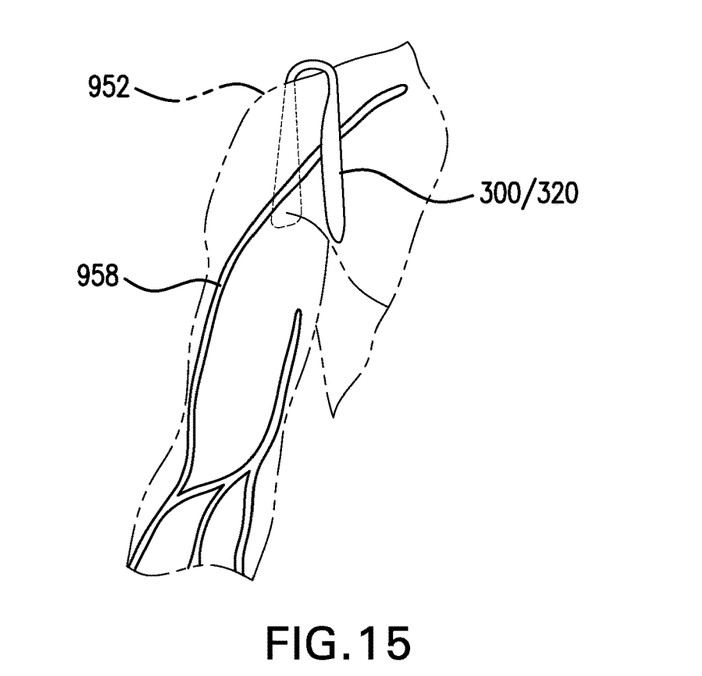
FIG. 15 shows a C-tourniquet in relation to the veins of the shoulder.
Figure 16:
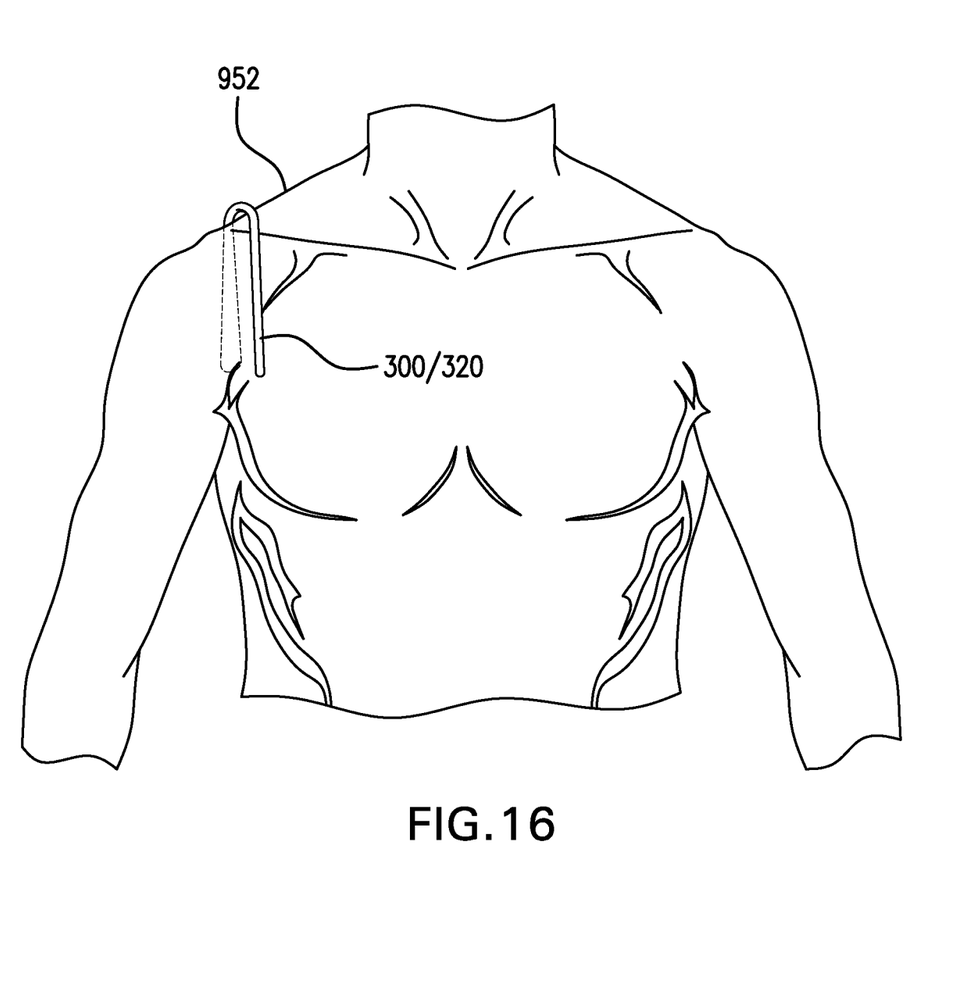
FIG. 16 shows the C-Tourniquet or clamp on the shoulder.
Figure 17A:
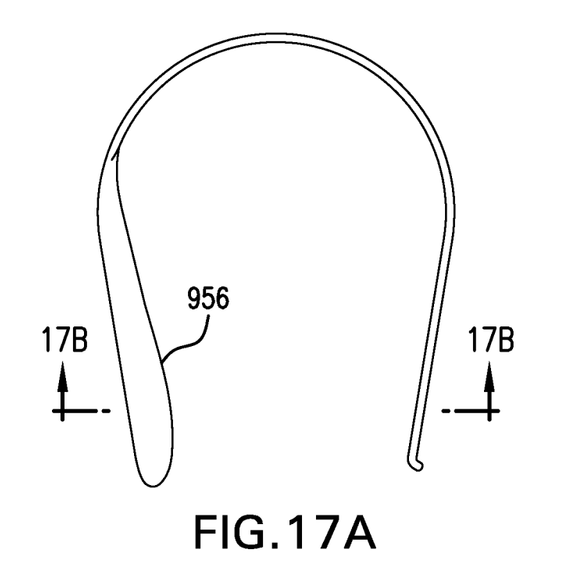
FIG. 17A through 17D depict an embodiment with a single sided clamp with a clamp member 956 on one side.
Figure 17B:
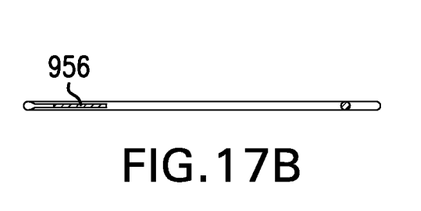
Figure 17C:
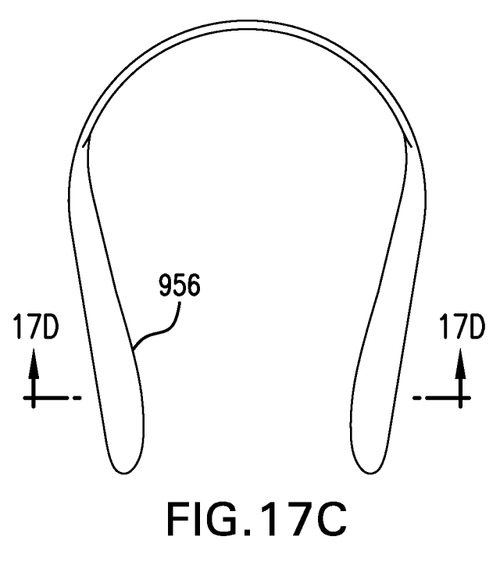
Figure 17D:
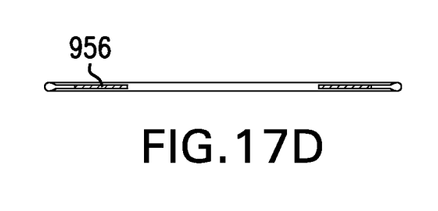
Figure 18A:
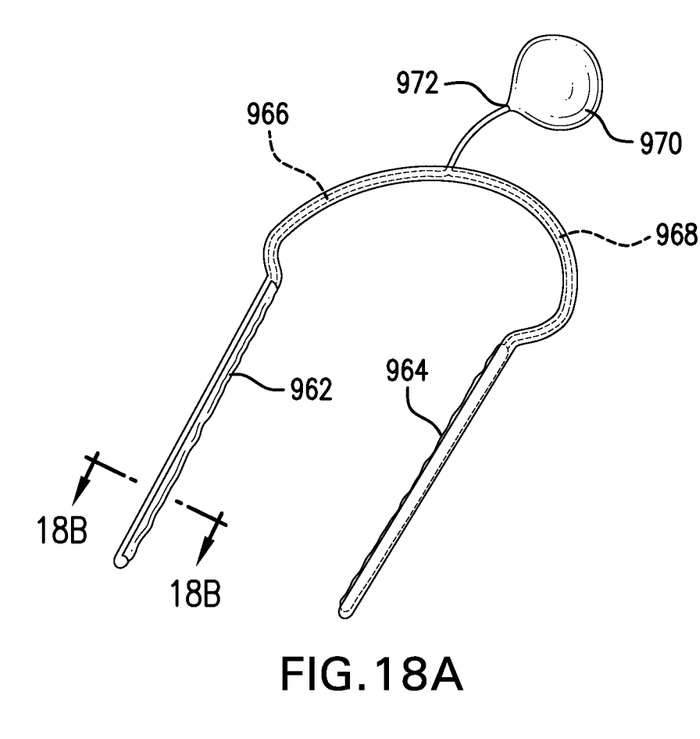
FIG. 18A through 18D show an embodiment with inflatable clamp members.
Figure 18B:
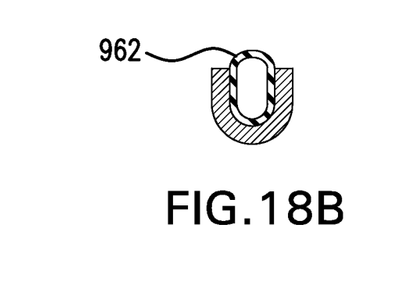
Figure 18C:
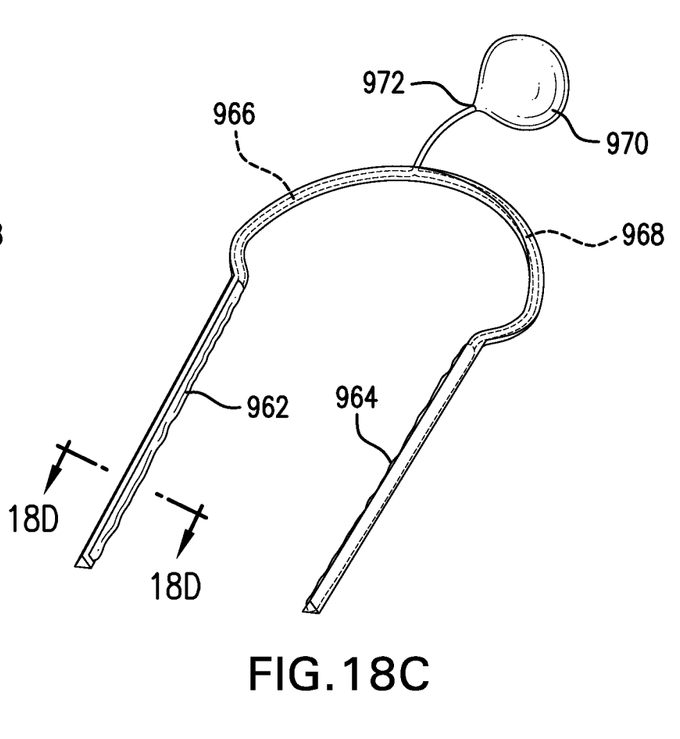
Figure 18D:
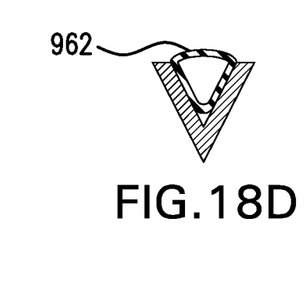

FIG. 14 depicts the veins of the shoulder and upper arm and, in particular, the cephalic vein 950. As shown in FIG. 15, the C-tourniquet 300/320 may be applied to across the shoulder 952 with the dashed lines representing the part of the device on the back side of the shoulder. FIG. 16 shows how this position of the C-tourniquet or claim 330/320 may appear without the veins being shown as applied to a shoulder 952.

FIG. 17 depicts an embodiment with a single sided clamp with a clamp member 956 on one side.

FIG. 18 shows an embodiments with inflatable clamp members 962 and 964 where the members can be inflated via air passages 966 and 968 using a finger operated pump 970 having a check valve.

Figure 19:
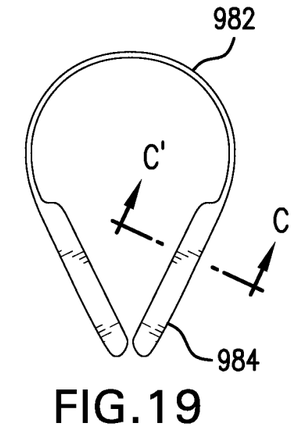
FIG. 19 depicts a C-tourniquet which is wider in the clamp area and where the clamp area is longer for better compression and adaptability to neck size variation.

FIG. 19 shows an embodiment in which the clamp members, such as 984, have been extended up the arms of the C-tourniquet. This allows the device to adapt to variations in neck size and location of the EJ and CV between patients. The device also allows for bilateral compression of the EJ veins.

Figure 20:
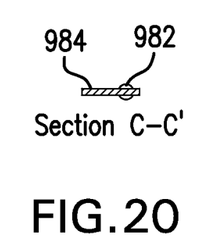
FIG. 20 shows a cross-section of FIG. 19.

FIG. 20 shows a cross-section from FIG. 19 viewed from the end of one arm. As can be seen the clamp member 984 has a flat aspect where the rod shape of the spring member 982 has been compressed. The rod has a round aspect and could be oval or rectangular.

Figure 21:
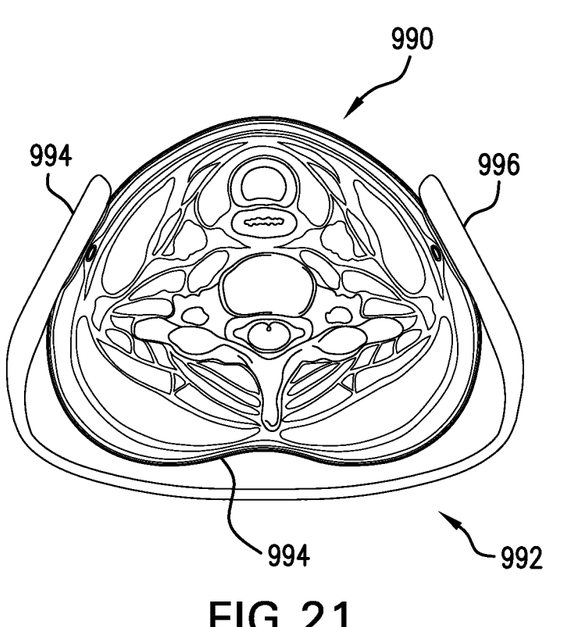
FIG. 21 shows another embodiment that is applied from the back of the neck.

FIG. 21 depicts a neck 990 where an embodiment of the C-tourniquet or clamp 992 may applied from the back 994. This embodiment has arms 994 and 996 that are bent toward the neck 990 and may have clamp members of the variations previously discussed, such as in FIG. 19.

Figure 22:
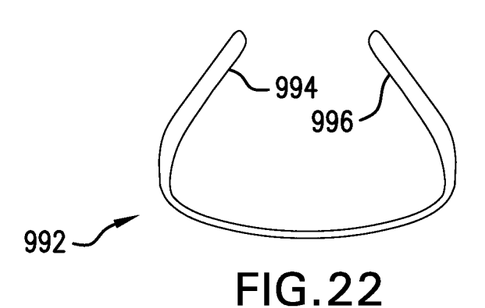
FIG. 22 shows the C-tourniquet of FIG. 21 when not applied.

FIG. 22 shows a shape the embodiment of FIG. 21 where the arms 994 and 996 are bent inward.

Although the C-clamp or C-tourniquet has been described as being made of injection molded plastic, it could be made of other materials that can provide a s spring force and tend to grip the neck, such as wire, resin reinforced paper, etc. as well as being made by another process, such as raise in the temperature of a plastic rod, using a heat source, such as a heat gun, until it is softens and can be formed, and then forming the clamp around an appropriately shaped mold. The clamp members have been generally been described as made of plastic so that they can be integrally formed with the spring member, however, the clamp members may be of another material, such as a foam or fabric pad. The surface of the clamp member may be roughened or corrugated or flat.

Figure 23:
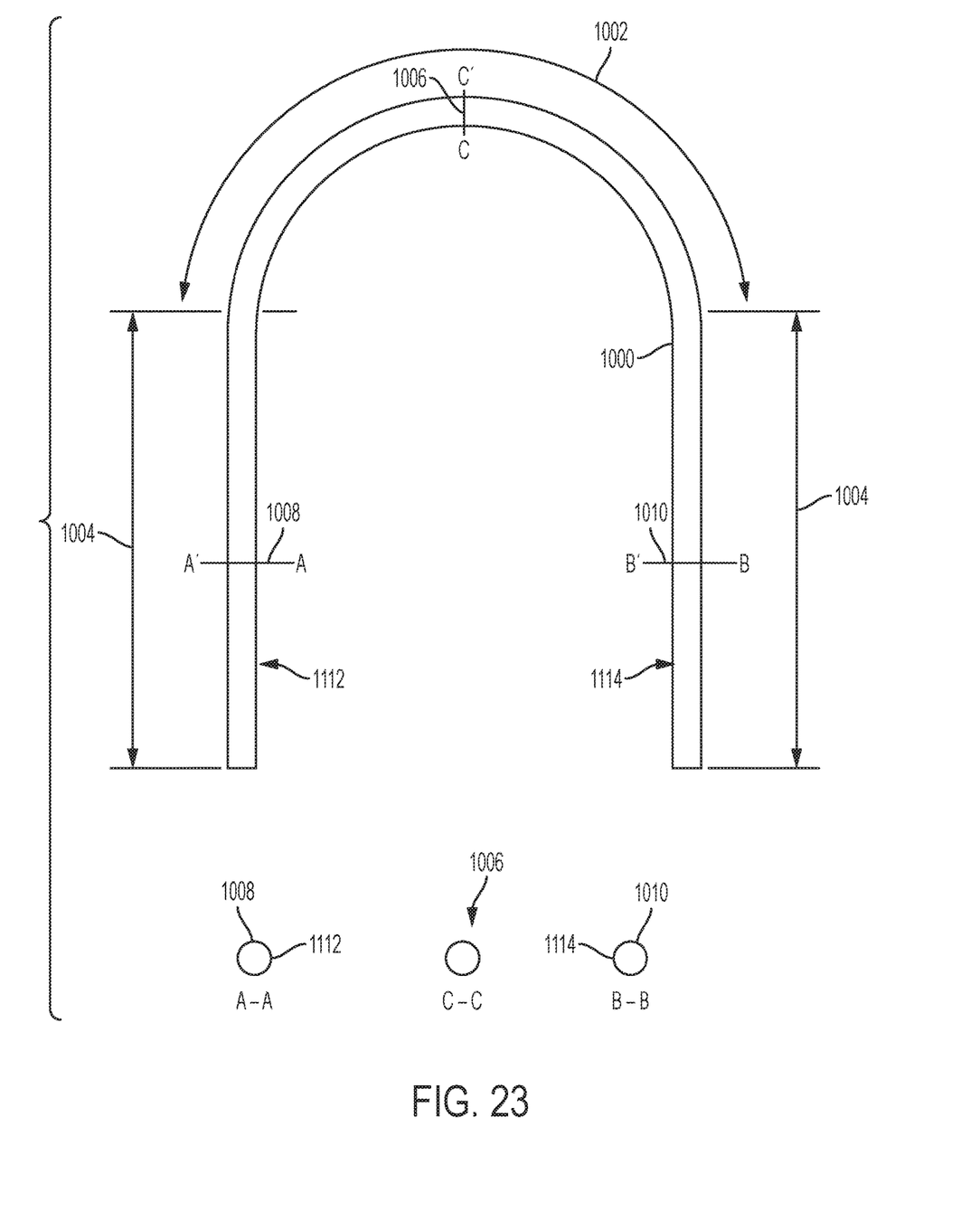
FIG. 23 shows a plastic rod C-Tourniquet.

FIG. 23 depicts a plastic rod C-Tourniquet 1000. The rod 1000 includes a spring section 1002 and clamp sections 1004. The spring section 1002 has a constant round cross C'-C 1006. The spring members 1004 also have constant round cross sections A'-A 1008 and B'-B 1010. Each rod end of the clamp members 1004 may have a rounded end to avoid scratching the patient as the C-Tourniquet is applied to a human neck or shoulder vein of the patient. One or both of inside, curved lateral sides 1112 or 1114 of the round cross section of the clamp members typically confronts the human neck or shoulder vein of the patient.

What is claimed is:

1. A human blood vessel compression device, comprising:
a plastic rod comprising:
   a C-shaped plastic spring member providing a spring closing force and having a constant round spring member cross section; and
   a plastic clamp member integrally extending from an end of the C-shaped spring member to compress one of a human neck vein and a human shoulder vein blood vessel, the plastic clamp member including a cross section part that is continuous with an inside, curved, lateral side that is continuous to confront the vein, and
wherein an area of the plastic clamp member is larger at the cross section part than a remaining area of the plastic clamp member.

2. A device as recited in claim 1, wherein the plastic clamp member further comprises includes an edge portion.

3. A device as recited in claim 1, wherein the device is configured to be positioned on a front of a neck near a base of the neck to allow the clamp member to confront an external jugular vein.

4. A device as recited in claim 1, wherein the device is configured to be positioned on a back of a neck to allow the plastic clamp member to confront an external jugular vein.

5. A device as recited in claim 1, wherein the device is configured to be positioned on a shoulder to allow the plastic clamp member to confront an external cephalic vein.

6. A device as recited in claim 1, wherein the C-shaped spring member further comprises a round cross section and first and second ends, and
   the plastic clamp member comprises first and second compression members further including edge portions.

7. A device as recited in claim 1, wherein the C-shaped spring member is configured to be spaced from a front of a neck to not compress a windpipe of the neck.

8. A device as recited in claim 1, wherein first and second compression members are oriented relative to the C-shaped spring member to extend toward a neck.

9. A device as recited in claim 1, wherein the C-shaped spring member further comprises:
   a round cross section and a first end, and
   the clamp member further includes a first compression member at the first end.

10. A blood vessel compression device, comprising:
a plastic rod, comprising:
   a plastic C-shaped spring member providing spring closing force and having a round cross section; and
   a plastic, round cross section clamp member integrally extending from an end of the plastic C-shaped spring member to compress one of a human neck and human shoulder vein blood vessel using an inside, lateral curved side of the plastic round cross section clamp member that is of a continuous structure,
wherein an area of the plastic, round cross section clamp member is larger at an edge part thereof than a remaining area of the plastic, round cross section clamp member.

11. A device as recited in claim 10, wherein the spring member and the clamp member comprise a single plastic rod.

12. A blood vessel compression device, comprising:
a plastic rod, comprising:
   a round cross section C-shaped spring member providing a spring force; and
   a round cross section clamp member integrally extending from the round cross section C-shaped spring member with a round, inside, lateral side configured to be continuous to compress one of a human neck and human shoulder vein blood vessel,
wherein an area of the round cross section clamp member is larger at an edge part thereof than a remaining area of the round cross section clamp member.

13. A device as recited in claim 12, wherein the spring member and the clamp member comprise a single plastic rod.

14. A blood pressure compression device, comprising:
a plastic rod, comprising:
   a C-shaped spring member configured to provide a spring force and having a constant round spring member cross section; and
   a clamp member integrally extending from an end of the C-shaped spring member, the clamp member including a cross section with a round, inside, lateral side that is continuous to compress one of a human neck and human shoulder blood vessel,
wherein an area of the clamp member is larger at an edge part of the cross section than a remaining area of the clamp member.

15. A blood pressure compression device, comprising:
a C-shaped plastic rod having a round cross section, the C-shaped plastic rod including:
   a spring section, and
   a clamp section integrally extending from an end of the spring section, the clamp section having a cross section that is continuous and having a round, inside, lateral side which is configured to compress one of a human neck and human shoulder vein blood vessel,
wherein an area of the clamp section is larger at an edge part of the cross section than a remaining area of the clamp section.

16. A device as recited in claim 15, wherein the plastic rod is configured to be positioned on a human neck spaced from a front of the neck to not compress a wind pipe of the neck.

17. A blood vessel compression device, comprising:
a U-shaped plastic rod comprising:

a rod spring section of the plastic rod with a round spring cross section configured to have a spring force; and a rod clamp section integrally extending from the rod spring section and having a round clamp cross section, wherein the spring force of a lateral curved side of the rod clamp section that is continuous is configured to compress one of a human neck vein and shoulder vein to swell the vein allowing cannula insertion into the vein using two hands, wherein an area of the clamp section is larger at an edge portion than a remaining area of the clamp section.

* * * * *